United States Patent [19]

Feinberg et al.

[11] Patent Number: 5,635,376
[45] Date of Patent: Jun. 3, 1997

[54] METHOD FOR PURIFYING CHROMOSOMES AND HYBRID MUNTJAC CELL LINES CONTAINING FOREIGN CHROMOSOMES

[75] Inventors: Andrew P. Feinberg, Lutherville; Jae-Yong Lee, Baltimore, both of Md.

[73] Assignee: The Regents of the University of Michigan, Ann Arbor, Mich.

[21] Appl. No.: 235,276

[22] Filed: Apr. 29, 1994

[51] Int. Cl.$^6$ .............................. C12P 19/34; C12N 5/10; C12N 5/26; C12N 15/64
[52] U.S. Cl. .................. 435/91.1; 435/172.3; 435/346; 435/325
[58] Field of Search .................. 435/6, 91.1, 172.2, 435/172.3, 240.2, 240.26, 820

[56] References Cited

PUBLICATIONS

Bouffler et al, *Somatic Cell and Molecular Genetics*. vol. 16, pp. 451–460 (1990).
Farr et al, *Proc. Natl. Acad. Sci. USA*, vol. 88, pp. 7006–7010 (1991).
Godfrey et al, *Mutation Research, DNA Repair*, vol. 274, pp. 225–235 (1992).
Hastie et al, *Trends in Genetics*, vol. 5, pp. 326–331 (1989).
Hatanaka et al, *The Journal of Experimental Medicine*, vol. 150, pp. 1195–1201 (1979).
Jha et al, *Mutation Research*, vol. 254, pp. 13–25 (1991).
Lee et al, *Cytogenet Cell Genet*, vol. 63, pp. 156–159 (1993).
Musk et al, *Biochimica et Biophysica Acta.*, vol. 1052, pp. 53–62 (1990).
Musk et al, *Mutation Research*, vol. 300, pp. 111–117 (1993).
Park et al, *Am. J. Hum. Genet.*, vol. 50, pp. 914–923 (1992).
Pillidge et al, *Mutation Research*, vol. 166, pp. 265–273 (1986).
Pillidge et al, *Int. J. Radiat. Biol.*, vol. 50, pp. 119–136 (1986).
Yamaguchi et al, *J. Gen Virol.*, vol. 42, pp. 289–296, (1979).
Yuasa et al, *Gann.*, vol. 69, pp. 441–445 (1978).
Experimental Cell Research, vol. 185, No. 1, pp. 101–108, 1989, C. Besnard, et al., "Reversible Extinction of Insulin Gene Expression in Insulinoma X Fibroblast Somatic Cell Hybrids".
Molecular and Cellular Biology, vol. 10, no. 12, pp. 6664–6673, Dec. 1990, T.E.W. Riley, et al., "Maintenance of Cellular Proliferation by Adenovirus Early Region 1A in Fibroblasts Conditionally Immortalized by Using Simian Virus 40 Large T Antigen Requires Conserved Region 1".
Experimental Cell Research, vol. 162, no. 2, pp. 530–538, Feb. 1986, L.V. Mayne, et al., "Efficient Immortalization and Morphological Transformation of Human Fibroblasts by Transfection with SV40 DNA Linked to a Dominant Marker".
Nature Genetics, vol. 7, No. 1, pp. 29–33, May 1994, J.Y. Lee, et al., "Simple Purification of Human Chromosomes to Homogeneity Using Muntjac Hybrid Cells".
Barthold: et al., *Methods in Enzymology*, vol. 151, 1987, pp. 252–267.
Levy et al., *Cytometry*, vol. 12, 1991, pp. 695–700.
Gunby et al. *Somatic Cell and Molecular Genetics*, vol. 13, 1987, pp. 245–252.
Chang et al., *Experimental Cell Research*, vol. 167, 1986, pp. 407–416.
Bouffler et al., *Journal of Cell Science*, vol. 91, 1988, pp. 423–429.
Atencio et al., *Journal of Virology*, vol. 67, 1993, pp. 1424–1432.

(List continued on next page.)

*Primary Examiner*—James S. Ketter
*Attorney, Agent, or Firm*—Oblon, Spivak, McClelland, Maier, & Neustadt, P.C.

[57] ABSTRACT

Introducing a chromosome or chromosome fragment having a size of 25 to 500 Mb and containing a selectable marker into a female muntjac cell which has been immortalized with a nonviral vector, a chemical treatment, or a radiation treatment permits the easy purification of the chromosome or chromosome fragment.

33 Claims, 6 Drawing Sheets

PUBLICATIONS

Saxon et al., *Methods in Enzymology*, vol. 151, 1987, pp. 313–325.

Bertsche et al., *Biochimica et Biophysica Acta*, vol. 939, 1988, pp. 509–522.

Darnell et al., *Molecular Cell Biology*, 1990, 2nd ed., Scientific American Books, New York, p. 322.

FIG. 4

METHOD FOR PURIFYING CHROMOSOMES AND HYBRID MUNTJAC CELL LINES CONTAINING FOREIGN CHROMOSOMES

BACKGROUND OF THE INVENTION

1. Field of the Invention

The present invention relates to immortalized female muntjac cell lines, a method for purifying nonmuntjac chromosomes utilizing such cell lines, and hybrid muntjac cell lines containing nonmuntjac chromosomes or chromosome fragments.

2. Discussion of the Background

Chromosome sorting is a powerful technique for gene mapping and isolation, but it has remained largely within the purview of few specialized centers. Furthermore, despite the successful generation of several highly purified chromosome-specific cosmid libraries (Deaven, L. L., *Cold Spring Harbor Symposia on Quantitative Biology*, Vol. L1, pp. 159–167 (1986); Fuscoe, J. C., Cytogenet. Cell Genet., Vol. 43, pp. 79–86 (1986); and Van Dilla, M. A., Cytometry, Vol. 11, pp. 208–218 (1990)), the ability to generate pure single chromosome fractions has generally been limited. Historically, rodent cell lines have been used for generating hybrid cell lines prior to chromosome purification, because of the relatively large number of mutant cell lines enabling selection (Ruddle, F. H., *Ann. Rev. Genet.*, Vol. 9, pp. 407–486 (1981)). However, with few exceptions, rodent cell lines contain chromosomes of the approximate size of most donor chromosomes, thus requiring specialized techniques and limiting the purity of the resulting sorted chromosomes (Fuscoe, J. C., *Cytogenet. Cell Genet.*, Vol. 43, pp. 79–86 (1986); and Van Dilla, M. A., Cytometry, Vol. 11, pp. 208–218 (1990)).

Thus, most of the libraries containing human chromosomes contain significant impurities. For example, a summary of the gene libraries for each chromosome available to the general public reveals that the hamster impurity in these libraries ranges from 11% to 55%, with an average impurity of 31.9% (Van Dilla, M. A., et al, *Cytometry*, vol. 11, pp. 208–218 (1990)).

Chromosome separations based on size have been attempted previously by zonal rotor centrifugation (Stubblefield, E., *Cytometry*, Vol. 2, pp. 273–281 (1991)), swinging bucket centrifugation (Mendelsohn, J., *J. Mol. Biol.*, Vol. 32, pp. 101–112 (1968)), or velocity sedimentation in specialized chambers (Collard, J. G., *Exp. Cell Res.*, Vol. 130, pp. 217–227 (1980)). However, separation of human chromosomes to homogeneity was not successful until the advent of flow sorting of human monochromosome hybrids in rodent cells. Even then, flow sorting has required the use of specialized techniques and equipment available only in a small number of centers, such as multi-dimensional sorting (Langlois, R. G., *Proc. Natl. Acad. Sci. USA*, Vol. 79, pp. 7876–7880 (1982)), pulse-shape flow cytometry (Bartholdi, M. F., *Cytometry*, Vol. 11, pp. 165–172 (1990)), fringe-scan (Mullikin, J., *Cytometry*, Vol. 9, pp. 111–120 (1988)), or slit-scan flow cytometry (Lucas, J. N., *Cytometry*, Vol. 8, pp. 273–279 (1987)), and computer aided analysis (van den Engh, G., *Cytometry*, Vol. 11, pp. 173–183 (1990)). With some exceptions, the resulting sorted chromosomes are still relatively impure, because of the similarity in size to one or more rodent chromosomes (Deaven, L. L., Cold Spring Harbor Symposia on *Quantitative Biology*, Vol. L1, pp. 159–167 (1986); Fuscoe, J. C., *Cytogenet. Cell Genet.*, Vol. 43, pp. 79–86 (1986); and Van Dilla, M. A., *Cytometry*, Vol. 11, pp. 208–218 (1990)).

The Indian muntjac, a small Asian barking deer, has the fewest diploid chromosomes of all mammals (Wurster, D. H., *Science*, Vol. 168, pp. 1364–1366 (1970)), with only 6 chromosomes (1,2,X) in the female and 7 in the male (1,2,X,Y), and the single laser, bivariate flow sorting of Indian muntjac chromosomes has been reported (Levy, H. P., et al, *Cytometry*, vol. 12, pp. 695–700 (1991)). Indian muntjac cells have been transformed for tumorigenicity studies with murine sarcoma virus (MSV) (Yuasa, Y., *Gann*, Vol. 69, pp. 441–445 (1978); and Hatanaka, M., *J. Expt. Med.*, Vol. 150, pp. 1195–1201 (1979)), avian sarcoma virus (ASV) (Yuasa, Y., *Gann*, Vol. 69, pp. 441–445 (1978)), and SV40(Yamaguchi, N., *J. Gen. Virol.*, Vol. 42, pp. 289–296 (1979)), but long-term karyotypic stability was not established (Yuasa, Y., *Gann*, Vol. 69, pp. 441–445 (1978); Hatanaka, M., *J. Expt. Med.*, Vol. 150, pp. 1195–1201 (1979); and Yamaguchi, N., *J. Gen. Virol.*, Vol. 42, pp. 289–296 (1979)).

One immortalized male muntjac cell line has been reported (Pillidge, L., et al, *Int. J. Radiat. Biol.*, vol. 50, pp. 119–136 (1986)). However, this cell line is so unstable that it is used as a model of karyotypic instability and defective DNA repair mechanisms (Pillidge, L., et al, *Mutation Research*, vol. 166, pp. 265–273 (1986); Bouffler, S. D., et al, *Somatic Cell and Molecular Genetics*, vol. 16, pp. 451–460 (1990); Musk, S. R. R., et al, *Biochimica et Biophysica Acta*, vol. 1052, pp. 53–62 (1990); Jha, B., et al, *Mutation Research*, vol. 254, pp. 13–25 (1991); Godfrey, D. B., et al, *Mutation Research*, vol. 274, pp. 225–235 (1992); and Musk, S. R. R., et al, *Mutation Research*, vol. 300, pp. 111–117 (1993)).

A readily available non-immortalized cell strain, from a male, contains a Y chromosome of comparable size to human group C chromosomes (American Type Culture Collection, *Catalogue of Cell Lines and Hybridomas*, Ed. 7 Rockville, Md.: American Type Culture Collection, p. 89 (1992)).

SUMMARY OF THE INVENTION

Accordingly, one object of the present invention is to provide novel stabile immortalized female muntjac cell lines.

It is another object of the present invention to provide a method for preparing such immortalized female muntjac cell lines.

It is another object of the present invention to provide novel hybrid muntjac cells which contain the normal complement of female muntjac chromosomes and a nonmuntjac chromosome or nonmuntjac chromosome fragment, in which the nonmuntjac chromosome or nonmuntjac chromosome fragment has a size of 25 to 500 Mb.

It is another object of the present invention to provide novel muntjac hybrid cell lines which contain the normal complement of female muntjac chromosomes and human chromosomes or a human chromosome fragment.

It is another object of the present invention to provide a method for purifying a chromosome or chromosome fragment which has a size of 25 to 500 Mb.

It is another object of the present invention to provide a method for purifying human chromosomes or human chromosome fragments.

It is another object of the present invention to provide a method for purifying chromosomes and chromosome fragments which does not require specialized equipment and can be conveniently carried out in most laboratories.

These and other objects, which will become apparent during the following detailed description, have been achieved by the inventor's discovery that individual chromosomes or chromosome fragments having a size of 25 to 500 Mb can be transferred readily to immortalized female muntjac cell lines, and that they can be purified to apparent homogeneity from the resulting hybrids using conventional equipment, such as unenhanced flow cytometry or preparative centrifugation, due to the great size difference between the chromosome or chromosome fragment to be purified and the muntjac chromosomes. The abundance, purity, speed and low cost of this approach makes direct chromosome purification a generally useful strategy for genome enrichment.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Thus, in a first embodiment, the present invention provides novel immortalized female muntjac cell lines. For the purposes of the present invention, it is important that the immortalized cell line be of female cells. The muntjac Y chromosome is much smaller than muntjac chromosomes 1, 2, and X. As explained in more detail below, the utility of the present immortalized muntjac cell lines resides their use in preparing the present hybrid cells which are useful in the present method for purifying chromosomes or chromosome fragments which in turn relies in part in the great size difference between the muntjac chromosomes and the chromosome or chromosome fragment to be purified. Since the muntjac Y chromosome is comparable in size to the chromosome or chromosome fragment to be purified, it is important that the immortalized cell line not contain any muntjac Y chromosome.

The immortalized female muntjac cell lines of the present invention have a normal female karyotype of 2n=6 and are karyotypically stable for long periods of time. In the context of the present invention, the term karyotypically stable for long periods of time means that the immortalized female muntjac cells retain the normal female karyotype of 2n=6 for at least 3 months, preferably at least 18 months. Since culturing such cells will normally involve a passage every 3.5 days, the immortalized female muntjac cells of the present invention are karyotypically stable for at least 15 passages, preferably at least 100 passages. In the context of the present invention, passage is defined as growing the cells to subconfluence, trypsinizing with tryspin (no EDTA), resuspending the cells, diluting them in media, and replating. Passage is performed at serial 1:5 dilutions (typical). Since the doubling time is about a day, and the cells also take a day to settle down and grow after splitting, it takes about 3 and a half days per passage (a year for 100 passages).

Another important feature of the present immortalized muntjac cell lines is that they not be immortalized by viral transformation. Muntjac cell lines which have been immortalized by viral transformation are unsuitable for use in the present methods because they shed viral particles. In addition, all efforts at immortalizing female muntjac cells with viruses, have led to chromosomal instability. It is also desired to transform as "minimally" as possible, because tumor lines in general are karyotypically unstable. There are two instability problems that can occur. First, too many chromosomes or fragmented muntjac chromosomes or rearranged chromosomes may occur. Second, the hybrids may not work well if the chromosomes are unstable, because the donor chromosomes tend to fragment or rearrange or more likely integrate into the muntjac chromosomes. Although integration occurs at late passages with all hybrids, it is likely to happen prior to sorting if the host chromosomes are from a tumor line or a "very transformed" line. Most importantly, if the muntjac line has fragments in it, it is unsuitable.

Thus, the present immortalized female muntjac cells may be produced by any conventional immortalization technique other than viral transformation. Examples of such techniques include, e.g., (A) treatment with a chemical (carcinogen), such as (1) 4-nitroquinoline-1-oxide (*Int. J. Cancer*, vol. 53(3), pp. 451–456 (1993)), (2) Benzopyrene (*Cancer Res.* vol. 52(8), pp. 2253–2256 (1992), and N-methyl-N'-nitro-nitrosoguanidine (*Cancer Res.*, vol 50(3), pp. 740–747 (1990); (B) exposure to Radiaion such as $^{60}$Co gamma rays (*J. Cancer Res. Clin Oncol.*, vol. 119(9), pp. 522–526 (1993); (C) transfection with a viral protein, such as (1) SV40 T antigen: pSV3gpt or pSV3neo (*J. Cell Physiol.*, vol. 150(1), pp. 158–167 (1992), or (2) E1A (*Exp. Cell. Res.*, vol. 182(2), pp. 559–571 (1989); and (D) transfection with an oncogene, such as v-myc, v-ras, v-raf/v-myc in retroviral vector (*Exp. Cell Res.*, vol. 201(2), pp. 273–283 (1992).

Good results have been achieved by transfection with a gene encoding a viral protein, and accordingly, transfection with pSV3gpt or pSV3neo is preferred. Transfection with pSV3gpt is particularly preferred. pSV3gpt is preferred over neo, because most existing cell lines containing a monochromosome (for donor into muntjac) are neo-tagged. But if a priori the tagging of the donor chromosomes is performed, then the choice of pSV3gpt is less important, so long as the muntjac and donor chromosome are tagged differently.

The present immortalized female muntjac cells may be prepared by subjecting any muntjac female diploid cell to one of the above-described immortalization techniques. Cells of the following tissue types may be suitably used include those from any tissue that grows in a monolayer (not circulating lymphocytes), but could be fibroblasts from any organ, or epithelial cells from any organ. Good results have been achieved using fibroblast cells, and the use of such cells is preferred. In addition, the present inventor has discovered that the use of cells obtained from a new-born female muntjac greatly facilitates the production of immortalized female muntjac cells having the normal female karyotype (2n=6) and which are karyotypically stable for long periods of time. By new-born muntjac, it is meant a muntjac which is less than 30 days old, preferably less than 7 days old.

The immortalized female muntjac cells of the present invention may be cultured on any conventional medium suitable for culturing immortalized eukaryotic cells. Examples of such media include Dulbeus's modified Eagles' medium with 20% fetal calf serum, MEM (minimal essential medium), Ham's F10, and Ham's F12. Suitable culture conditions are 35 to 38° C., preferably 36.5° to 37.5° C. It is also important that the medium contain about 5% $CO_2$, and an antibiotic such as penicillin or streptomycin. The cells are maintained at an appropriate cell density, 10–90% confluence, and at not too late a passage (<100, preferably 30).

The immortalized female muntjac cells are useful for producing hybrid muntjac cells which contain, in addition of the muntjac female chromosomes, a nonmuntjac chromosome or nonmuntjac chromosome fragment. As noted above, the hybrid cells of the present invention are useful in the present method for purifying the nonmuntjac chromosome or nonmuntjac chromosome fragment. Since the present method of chromosome purification relies on the difference in size between the female muntjac chromosomes on the one hand and the nonmuntjac chromosome or nonmuntjac chromosome fragment on the other hand, the nonmuntjac chromosome and nonmuntjac chromosome fragment suitably have a size of 25 to 500 Mb, preferably 50 to 300 Mb. If the nonmuntjac chromosome or nonmuntjac chromosome fragment has a size greater than 500 Mb, it may be difficult to separate the nonmuntjac chromosome or nonmuntjac chromosome fragment from the female muntjac chromosomes by the methods described below. Depending on the quality of chromosome preparation, the preparation may contain muntjac chromosome fragments (more if a bad prep) about the same size as the smallest nonmuntjac chromosomes (e.g., human chromosomes 20–22, about 50 Mb). Thus, excellent preparations are required for purifying nonmuntjac chromosomes smaller than 25 Mb.

The nonmuntjac chromosome or nonmuntjac chromosome fragment must also contain a selectable marker. The selectable marker may be any selectable marker which can be introduced or occurs naturally on the chromosome but is not present in the female muntjac genome. For example, the selectable marker may be an antibiotic resistance gene transfected into the nonmuntjac chromosome or nonmuntjac chromosome fragment. Examples of such antibiotic resistance genes include neo which confers resistance to G418; hph which confers resistance to hygromycin; and gpt, which confers resistance to mycophenolic acid. In addition, auxotrophic markers such as his, lys, etc. may be used. The selectable marker may be introduced into the nonmuntjac chromosome or nonmuntjac chromosome fragment by any conventional technique. For example, neo may be introduced by way of pSV2neo or pCDneo.

The nonmuntjac chromosome or nonmuntjac chromosome fragment may be of any origin so long as it is within the above-discussed size range. For example, the nonmuntjac chromosome or nonmuntjac chromosome fragment may be obtained from human, mouse, rat, cat, dog, horse, pig, cow, avians, insects, other mammals and amphibians or other species. Preferably, the nonmuntjac chromosome or nonmuntjac chromosome fragment is of human origin.

The hybrid cells of the present invention may be obtained by introducing the nonmuntjac chromosome or nonmuntjac chromosome fragment having a size of 25 to 500 Mb, and containing a selectable marker, into the immortalized female muntjac cells of the present invention and then culturing the resulting cells under conditions under which only a cell which contains the selectable marker will survive. For the purposes of the present invention, it is important that the hybrid cells be formed by introducing the nonmuntjac chromosome or nonmuntjac chromosome fragment into the immortalized female muntjac cells of the present invention, rather than into a female muntjac cell strain.

The advantages of using an immortalized line as compared to a nonimmortalized line include:

1) A non-immortalized cell will senesce (so no experiment is possible).

2) A non-immortalized cell has a maximum population doubling of about 50 (13 passages, less about 5 inside the animal during embryogenesis before the cells are obtained).

3) Hybrids are needed for the present method, which requires even more passages after the introduction of the chromosome.

4) To purify chromosomes, it is necessary to grow up the hybrids to mass culture.

5) Reproducibility among all the hybrids and laboratories is facilitated by the use of an immortalized line.

6) In later passages (after 8 or 9) with a cell strain (i.e. non immortalized) cell growth slows down significantly. Immortalized lines grow rapidly forever.

The nonmuntjac chromosome or nonmuntjac chromosome fragment may be introduced into the immortalized female muntjac cells by any conventional technique, such as microcell fusion, cell fusion, chromosome-mediated gene transfer, and microinjection.

Good results have been achieved using microcell fusion, and accordingly, this method is preferred. Microcells, generally containing one chromosome each due to size filtration, are generated from cells which contain the nonmuntjac chromosome or nonmuntjac chromosome fragment. For example, a neomycin resistance gene, pSV2neo, may be introduced by transfection into a mouse microcell hybrid containing human chromosome 11. This gene integrates randomly into both the human chromosome (number 11 in this instance) and the many mouse chromosomes in the hybrid cell. This step generates hundreds or thousands of colonies containing neo at many different sites of integration into chromosome 11.

The second step is the selective transfer into immortalized female muntjac cells of the human chromosome 11 carrying the pSV2neo gene. For this step, 200 to 1,000 G418-resistant colonies from the first step are pooled (neomycin confers resistance of mammalian cells to the antibiotic G418). "Microcells", generally containing one chromosome each, are prepared from the whole cells within these pools. The microcells are then fused to the immortalized female muntjac cells using polyethylene glycol, and selection for surviving cells with G418 is performed. Two types of cells can result. First, recipient cells might not contain the human chromosome with neo. These will die in the presence of G418. Secondly, recipient cells may contain the human chromosome with neo, and only these cells will survive.

The exact culturing condition such that only a cell containing the selectable marker will survive will, of course, depend on the identity of the selectable marker. In the case of neo, the condition will be the presence of 100 to 1000 µg/ml, preferably 400 to 800 µg/ml, of G418 in the culture medium. In the case of hph, the condition will be the presence of 20 to 100 µg/ml, preferably about 50 µg/ml, of hygromycin in the culture medium. In the case of gpt, the condition will be the presence of 10 to 50 µg/ml, preferably about 25 µg/ml, of mycophenolic acid in the culture medium. Otherwise any conventional culture medium, such as those described above in connection with the culturing of the immortalized cell lines, may be used.

The nonmuntjac chromosome or nonmuntjac chromosome fragment may be isolated from the other (female muntjac) chromosomes by any conventional technique, such as flow cytometry, gradient centrifugation, zonal rotor centrifugation, swinging bucket centrifugation, or centrifugal elutriation.

Thus, after the hybrid cells are lysed, the chromosomes may be isolated by any conventional method, such as the polyamine method. The isolated chromosomes may be stained with, e.g., propidium iodide and sorted using a flow cytometer. When using flow cytometry for chromosome sorting, a speed of 100 to 1,000,000, preferably 1,000 to 10,000, particles per minute may be used. Of course, other dyes, such as chromomycin, Hoechst, or actinomycin D may be used instead of propidium iodide.

Alternatively, the chromosomes from the hybrid cell may be sorted by means of gradient centrifugation. A suitable gradient is a 5–20 wt.% linear sucrose gradient. Suitably, the centrifugation is carried out at 10 to 500g, preferably 20 to 200 g, for 5 to 300 minutes, preferably 20 to 120 minutes.

The following discussion will describe the particular results obtained when the present invention is applied to the purification of specific human chromosomes and human chromosome fragments. This discussion is provided to further illustrate the present invention and, unless otherwise specified, does not limit the present invention.

Fibroblast cell lines were established from a skin biopsy taken from a newborn female Indian muntjac (see FIG. 1). Karyotyping of primary cell lines showed 6 diploid chromosomes as expected. Primary fibroblast cells were transfected with an origin defective SV40 vector, pSV3gpt and selected with mycophenolic acid (Mulligan, R. C., *Proc. Natl. Acad. Sci. USA*, Vol. 78, pp. 2072–2076 (1981)). Colonies surviving selection were further cultivated to obtain immortalized colonies after crisis. Nine colonies were obtained and karyotyped. Three cell lines were diploid, 3 were a mixture of diploid and tetraploid cells, and 3 developed chromosomal rearrangements. One of the three diploid clones with a normal female karyotype (2n=6), was stable for over 18 months (100 passages).

Using this method, the following immortalized female muntjac cell line was obtained: FM7-1, FM7-2, and FM7-3.

One of these lines, FM7-1, has been depositied with the American Type Culture Collection, 12301 Parklawn Drive, Rockville, Md. 20852, under the provisions of the Budapest Treaty. FM7-1 was used in all further studies.

Figure 1A:
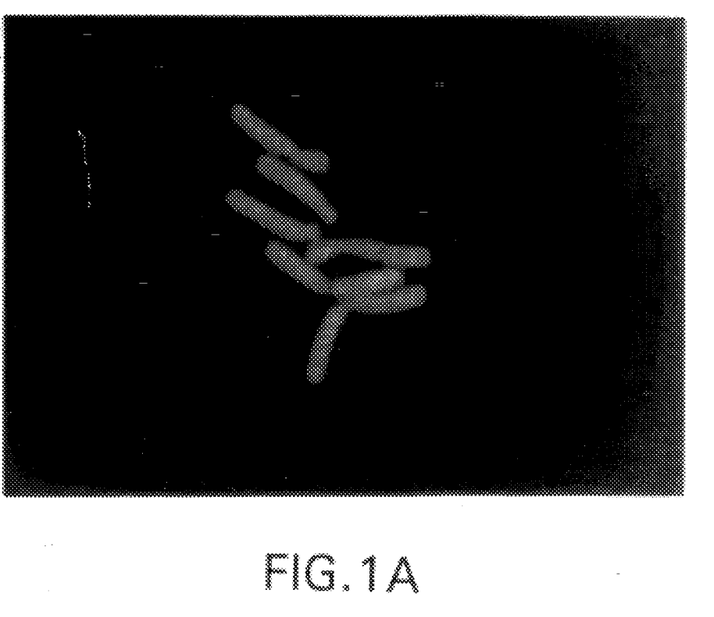
FIGS. 1a–d illustrate the fluorescence in situ hybridization of chromosomes from human monochromosome muntjac hybrids and purified human chromosomes, using total human DNA as a probe. (a) Immortalized female Muntjac cell line (FM7), showing diploid chromosome content of 6. (b) Human monochromosome muntjac hybrid cells (FM7-H11), demonstrating the approximately ten-fold difference in chromosomal size between the diploid muntjac chromosomes and the two copies of human chromosome 11. (c) Human chromosomes purified by flow sorting from the hybrid. All of the chromosomes are of human origin. (d) Human chromosomes purified from hybrid cells by sucrose gradient centrifugation. All of the chromosomes are of human origin. Chromosomes were purified as described in the Examples below, fixed in methanol-acetic acid (3:1) and stained with propidium iodide (red). Human chromosomes (green) were visualized by hybridization with a biotinylated (BRL) Alu probe (Deininger, P. L., *J. Mol. Biol.*, Vol. 151, pp. 17–33 (1981)), incubation with FITC-avidin and amplification with anti-avidin antibody (Oncor)
Figure 1B:
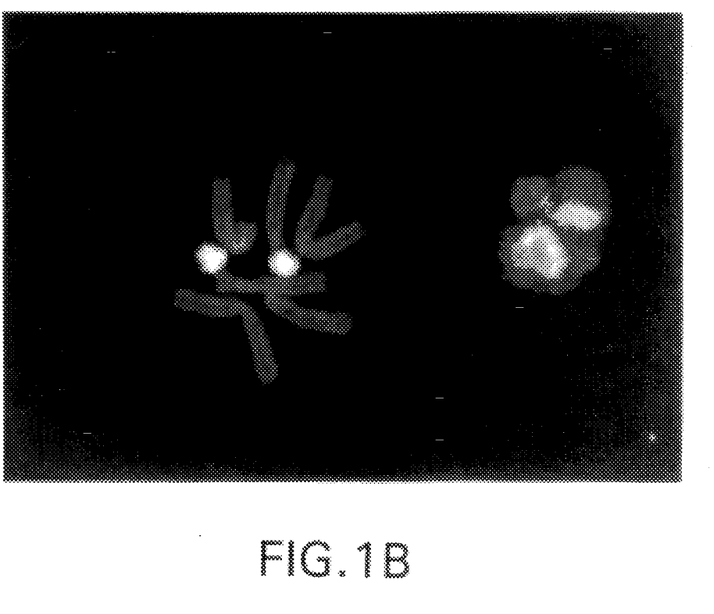

Neo was chosen as a selectable marker for monochromosome transfer because of the availability of neo-containing monochromosome hybrids for most human chromosomes. However, since monochromosome transfer to muntjac cells had not been attempted previously, it was important to demonstrate whether the muntjac chromosomes were suitable recipients by microcell fusion, as well as to determine the ease of generation and stability of the hybrids obtained. A derivative of chromosome 11 reported earlier (Koi, M., *Science*, Vol. 260, pp. 361–364 (1993)) was transferred into the FM7 muntjac cell line by microcell fusion (Koi, M., *Jpn. J. Cancer Res.*, Vol. 80, pp. 413–418 (1989); Fournier, R. E. K., *Proc. Natl. Acad. Sci. USA*, Vol. 74(1), pp. 319–323 (1977); and Saxon, P. J., *Mol. Cell. Biol.*, vol. 5, pp. 140–146 (1985)). Ten neo-resistant isolates were obtained, and karyotyping confirmed the presence of six giant muntjac chromosomes and a small additional chromosome resembling human chromosome 11. Two isolates were further cultivated and assayed for karyotypic stability. Both cell lines were stable over 30 passages. The karyotype showed that all cells maintained the extra chromosome. In situ hybridization confirmed that the extra chromosome was of human origin (See FIGS. 1a and b), and quinacrine banding corroborated the presence of human chromosome 11. Three other human chromosomes, each containing the mammalian selectable marker gene pSV2neo: chromosome 20, chromosome 5, and a "subchromosomal transferable fragment" or STF (Koi, M., *Science*, Vol. 260, pp. 361–364 (1993)) from chromosome 11, were transferred to FM7. In all cases, the hybrids selected with G418 retained muntjac chromosomes 1,2,X, and the additional human chromosome, as shown by both flow karyotype analysis and/or in situ hybridization using total human DNA as a probe. Mouse chromosomes were never present in the derivative hybrids. Furthermore, hybrids with the larger human chromosomes were remarkably stable, with no change in karyotype over time, although as with conventional rodent cell hybrids (Koi, M., *Jpn. J. Cancer Res.*, Vol. 80, pp. 413–418 (1989)), integration of the two small chromosomes (20 and the STF) into muntjac DNA was observed at late passages (>30). In addition, as with conventional hybrids (Koi, M., *Jpn. J. Cancer Res.*, Vol. 80, pp. 413–418 (1989)), while the larger human chromosomes were present in all of the hybrid cells, the smaller chromosomes were seen in approximately half of cells.

In summary, chromosomes of varying size and an STF were all easily transferred to cell line FM7 by microcell fusion. Using these methods, the following hybrid cells have been obtained

| Designation | Nonmuntjac Chromosome or fragment |
| --- | --- |
| FM7-H11 | 11 |
| FM7-H20 | 20 |
| FM7-HSTF11 | STF of 11 |

FM7-H11, has been deposited with the American Type Culture Collection, 12301 Parklawn Drive, Rockville, Md. 20852, under the provisions of the Budapest Treaty.

In the case of human chromosome 5, long term viability was not observed for the FM7 hybrid (FM7-H5). This is due to an incompatibility between human chromosome 5 and cells immortalized with SV40 or T-antigen. Thus, in the case of human chromosome 5, the immortalized female muntjac cell line should be prepared by immortalization with a nonviral vector other than pSV3gpt or pSV3neo, such as E1A, or with any of the chemical, radiation, or oncogene transformations discussed above.

Figure 2A:
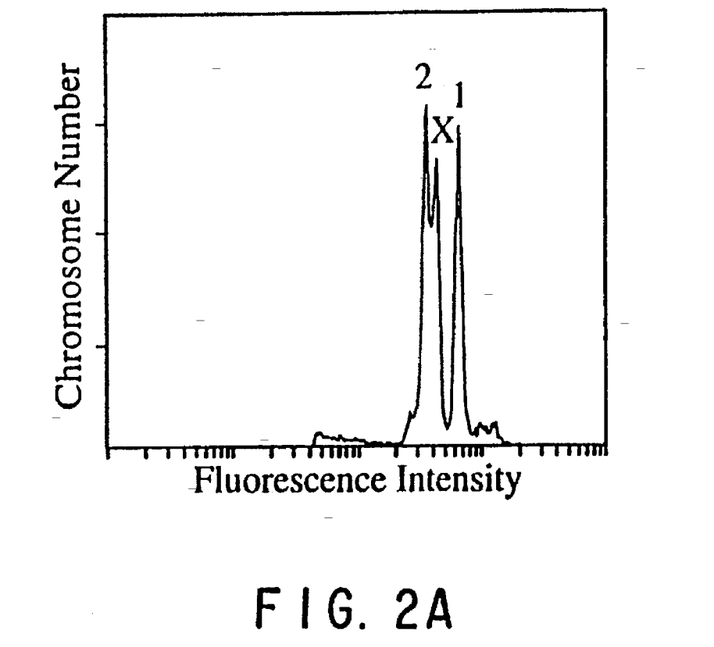
FIGS. 2a–d show the flow karyotype of a stable female Indian muntjac cell line (FM7), a human monochromosome hybrid derived from FM7, and human chromosomes purified from the hybrid by flow sorting or sucrose gradient centrifugation. (a) FM7 cells with a stable diploid chromosome content of 6; (b) Human-muntjac hybrid cells containing a derivative human chromosome 11; (c) Human chromosome 11 purified from the hybrid by flow sorting, demonstrating >95% homogeneity; and (d) Human chromosome purified from the hybrid by sucrose gradient centrifugation, demonstrating >90% homogeneity. Relative chromosome number is plotted in arbitrary arithmetic units as a function of the logarithm of fluorescence intensity. 1,2, and X refer to the female Muntjac chromosomes, and 11 to the human chromosome.
Figure 2B:
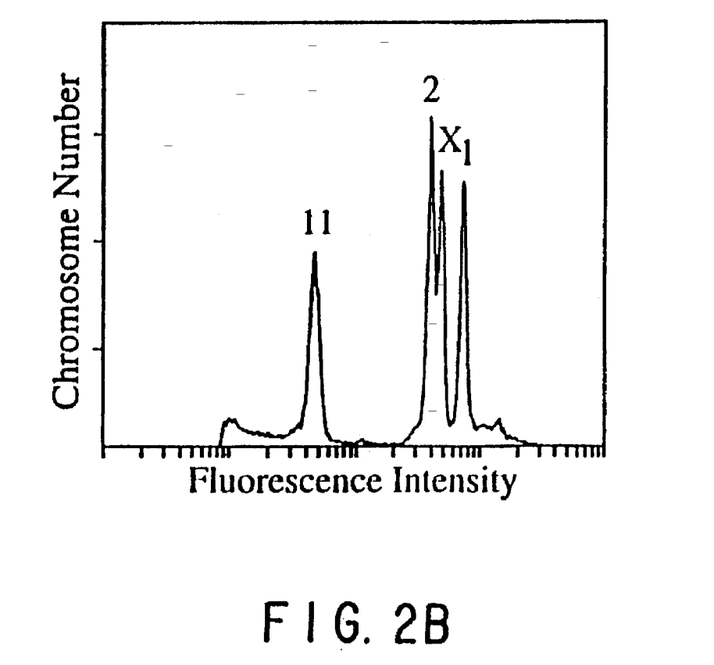

Because of the karyotypic simplicity and marked difference in size of the donor and host chromosomes, it seemed likely that one could purify that chromosome from the host background using ordinary skill and equipment. Total chromosomes were first isolated from hybrid cells using the polyamine method, in order to maintain DNA at high molecular weight (Cram, L. S., *Methods Cell. Biol.*, Vol. 33, pp. 377–381 (1990).), were stained with propidium iodide, and analyzed by flow cytometry. The immortalized female Indian muntjac cell line (FM7) showed three large chromosome peaks as expected (see FIG. 2a). The human chromosome 11-FM7 hybrid showed a well-separated additional chromosomal peak (see FIG. 2b). Using a conventional univariate flow cytometer for flow sorting, $4 \times 10^6$ human chromosomes were obtained, $10^4$ were analyzed by flow cytometry, $10^6$ were used for in situ hybridization, and $2 \times 10^6$ were analyzed by molecular hybridization.

Figure 1C:
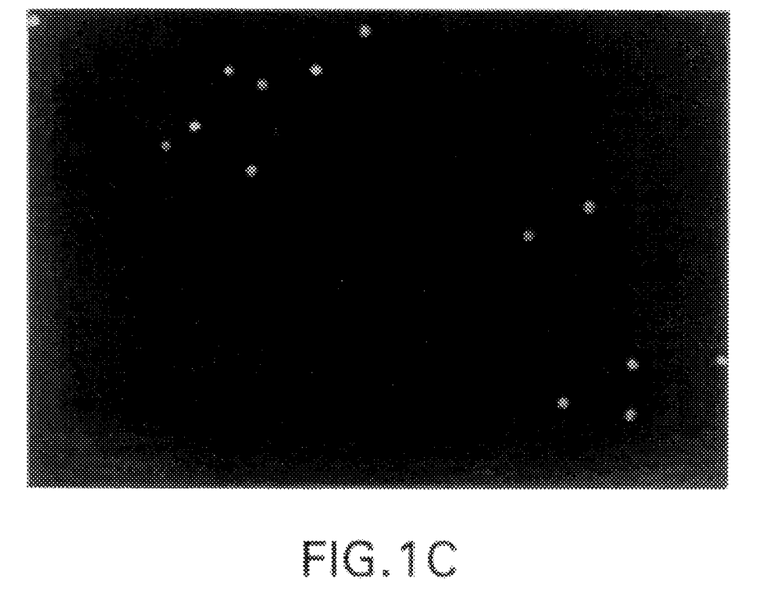
Figure 1D:
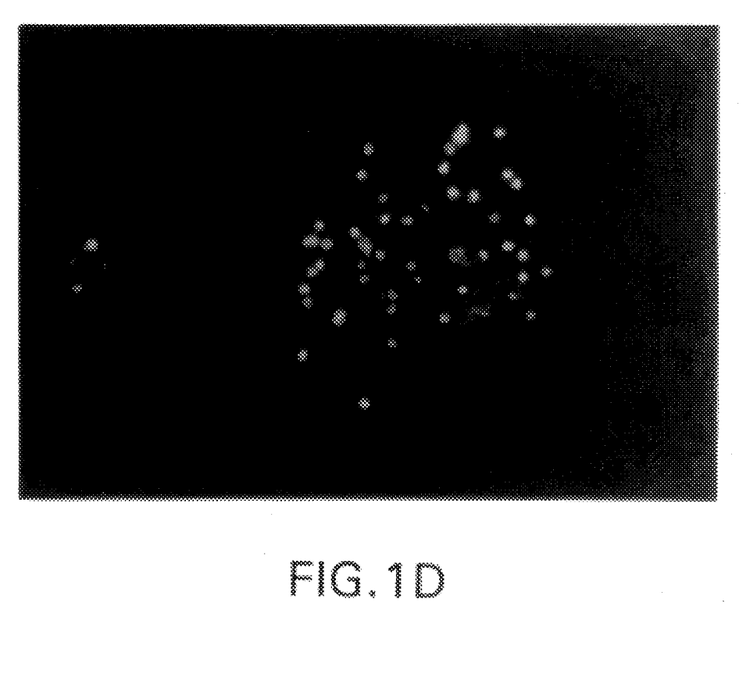
Figure 2C:
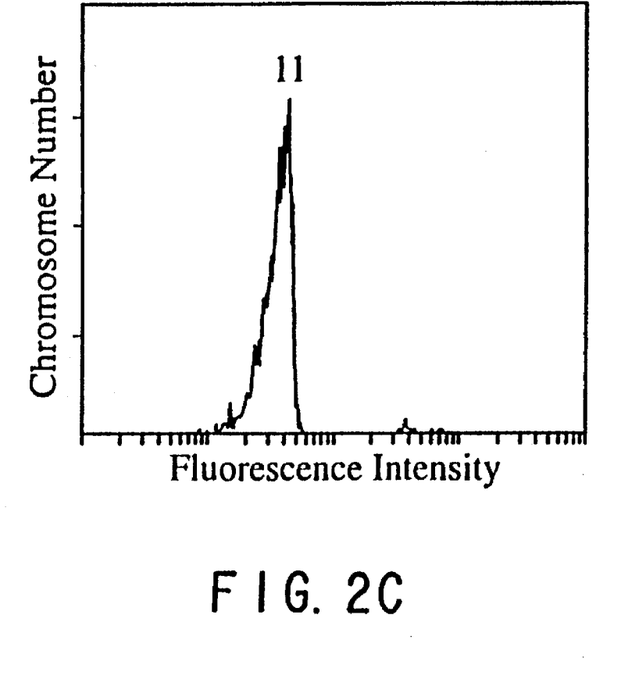

Flow karyotype analysis suggested quantitative separation (>95%) (see FIG. 2c), and this result has been consistent in over 30 trials of chromosome sorting. To exclude the possibility that the sorted material might represent chromosomal debris rather than the small human chromosome, in situ hybridization on both unsorted and sorted chromosomal fragments was performed. As shown in FIG. 1c, all of the sorted chromosomes fluoresced with a human repetitive DNA probe, indicating that the sorted chromosomes were pure.

Figure 2D:
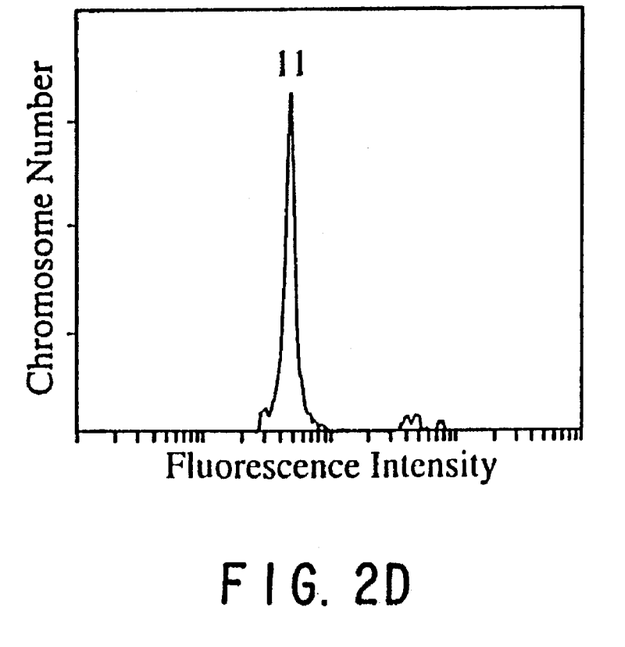

The marked size difference of the human and muntjac chromosomes suggested that a flow cytometer might not always be needed for chromosome purification. The human chromosome was thus isolated directly by preparative centrifugation, using a 5–20% linear sucrose gradient. Flow karyotype analysis and in situ hybridization demonstrated that the fractionated chromosomes were >90% pure (see FIGS. 1d and 2d), permitting purification of unlimited quantities of the chromosome using conventional laboratory instrumentation.

Figure 3:
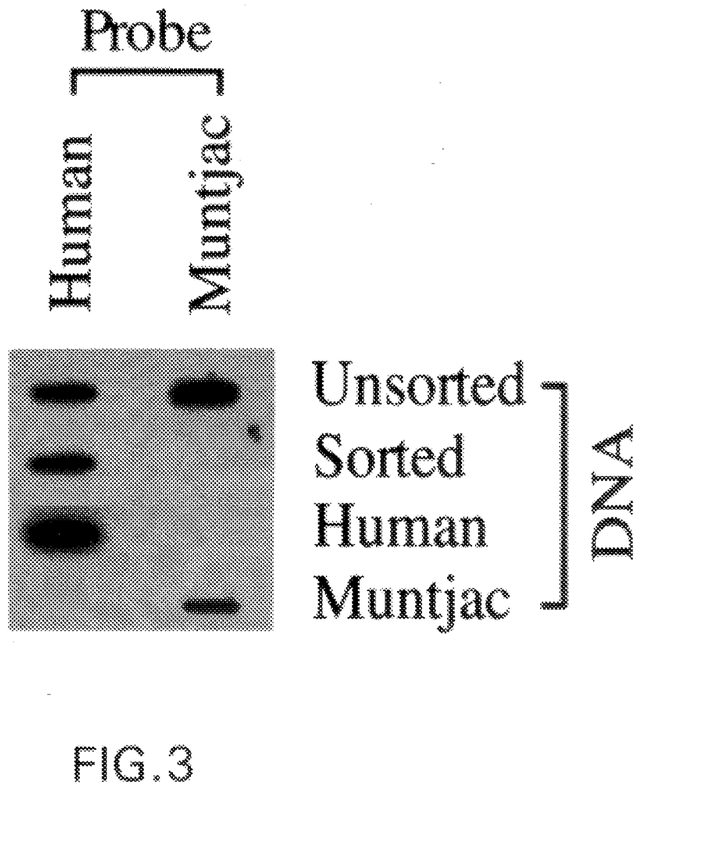
FIG. 3 shows the results of quantitative slot-blot analysis of unsorted and sorted chromosomes from muntjac/human hybrid cells. DNA was isolated from sorted and unsorted chromosomes, transferred by Southern blotting to a nylon filter, and hybridized using a human Alu probe or muntjac repeat probe. Human and muntjac genomic DNA was used as positive and negative controls for hybridization with human and muntjac probes.
Figure 4:
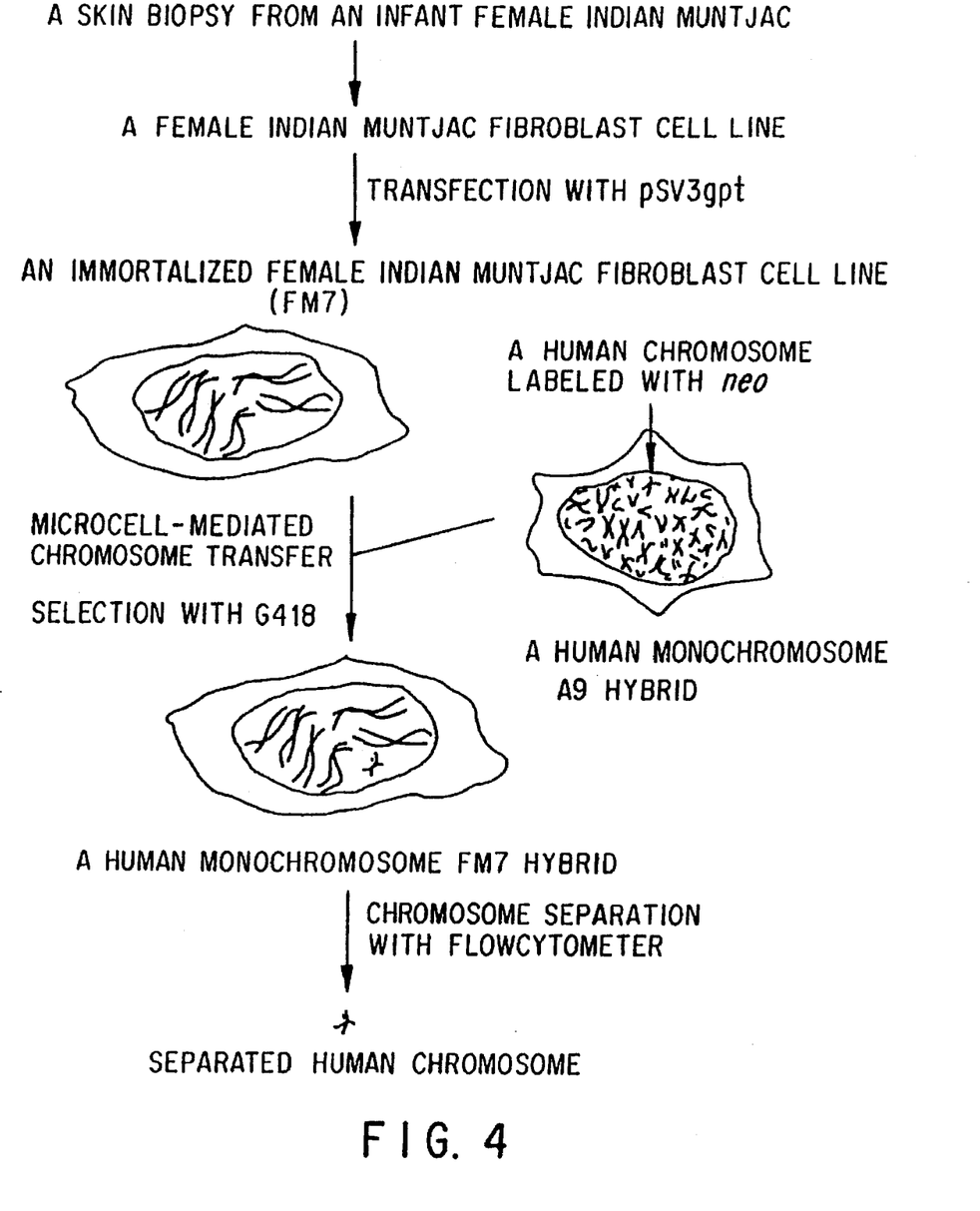
FIG. 4 shows a schematic flow chart for an embodiment of the present method.

Even though flow cytometry and in situ hybridization strongly suggested that the purification of human chromosomes was quantitative and homogeneous, definitive confirmation of this observation was sought by molecular analysis of extracted DNA from the individual sorted fractions. DNA was isolated from $10^6$ sorted human chromosomes and $10^6$ unsorted chromosomes and transferred to nylon filters. The human chromosomal fraction was quantitatively pure, as expected from previous results (see FIG. 3). Finally, to determine the size of the purified human DNA, $10^6$ were embedded in 1% low melting temperature agarose and electrophoresed under CHEF (clamped homogenous electric field) conditions using high molecular weight standards. This analysis revealed that the sorted human chromosomes were >1.6 Mb in size, within the ideal range for unsorted chromosome preparations (Trask, B., in *Flow Cytogenetics* (ed. Gray, J. W.) pp. 43–46 (Academic, New York, 1989)).

Other features of the invention will become apparent in the course of the following descriptions of exemplary embodiments which are given for illustration of the invention and are not intended to be limiting thereof.

EXAMPLES

I. Establishment and immortalization of a female Muntjac fibroblast cell line.

A fibroblast cell line was established from a skin biopsy of an infant female muntjac in α-MEM (modified Eagle medium) with 10% fetal bovine serum. In order to obtain an immortalized cell line, the fibroblast cell line was transfected by calcium phosphate precipitation (Graham, F. L., *Virology*, Vol. 52, pp. 456–467 (1973); and Wigler, M., *Cell*, Vol. 14, pp. 725–731 (1978)) with an origin-defective SV40 vector, pSV3gpt (Mulligan, R. C., *Proc. Natl. Acad. Sci. USA*, Vol. 78, pp. 2072–2076 (1981)) and selected DMEM (Dulbeco modified Eagle medium), 10% fetal bovine serum containing adenine (25 µg/ml), L-glutamine (15 µg/ml), thymidine (10 µg/ml), aminopterin (2 µg/ml) and mycophenolic acid (25 µg/ml) (Mulligan, R. C., *Proc. Natl. Acad. Sci. USA*, Vol. 78, pp. 2072–2076 (1981)). Primary resistant colonies were cloned and cultivated in DMEM with 10% fetal bovine serum to expand colonies after crises. Immortalized colonies were isolated and cultivated for more than 30 passages to confirm their stability. The karyotype of stable colonies was determined by quinacrine banding.

II. Preparation of human monochromosome female muntjac hybrid cells.

To prepare human monochromosome female muntjac cell hybrids, neo-tagged human monochromosome A9 hybrid cell lines were used as donors of chromosome 20 (Koi, M., *Jpn. J. Cancer Res.*, Vol. 80, pp. 413–418 (1989)), chromosome 5 (Goyette, M. C., *Mol. Cell. Biol.*, Vol. 12, pp. 1387–1395 (1992)), chromosome 11 (Koi, M., *Science*, Vol. 260, pp. 361–364 (1993)), and a human 11p15 fragment (Koi, M., *Science*, Vol. 260, pp. 361–364 (1993)). A9 hybrid cells were micronucleated in the presence of colcemid, and chromosomes were transferred to FM7 cells by microcell fusion with previously described techniques (Koi, M., Jpn. *J. Cancer Res.*, Vol. 80, pp. 413–418 (1989); Fournier, R. E. K., *Proc. Natl. Acad. Sci. USA*, Vol. 4(1), pp. 319–323 (1977); and Saxon, P. J., *Mol. Cell. Biol.*, vol. 5, pp. 140–146 (1985)). Colonies were selected for G418 resistance (400 µg/ml). About 10 colonies were picked for each monochromosome hybrid. Metaphase chromosomes from colonies were prepared on slides and analyzed by quinacrine banding. Chromosome stability was confirmed by karyotyping during cultivation for more than 20 passages. Stable lines were used for in situ hybridization analyses and chromosome preparation.

A. In situ hybridization. A biotinylated Alu probe was prepared by nick translation of a gel purified Alu fragment digested from BLUR8 (Deininger, P. L., *J. Mol. Biol.*, Vol. 151, pp. 17–33 (1981)) in the presence of biotin 14-dATP (BRL). Metaphase chromosomes were prepared on slides. The sorted chromosomes were fixed by washing three times with methanol-acetic acid (3:1) and dropped on glass slides. Human chromosomes were visualized by hybridization with the biotinylated Alu probe, incubation with FITC-avidin, and amplification with anti-avidin antibody (Oncor). All chromosomes were stained with propidium iodide and visualized under a Zeiss Axiophot fluorescence photomicroscope (250–1000x).

B. Chromosome preparation and purification. 80–90% confluent hybrid cells were incubated in DMEM with 10% fetal bovine serum, 400 µg/ml G418 and 0.1 µg/ml colcemid for 12–18 hours to induce mitotic arrest. Mitotic cells were detached by shaking and collected by centrifugation on a Beckman bench top centrifuge at 1800 rpm. Chromosomes were isolated by the polyamine method as described previously (Cram, L. S., *Methods Cell. Biol.*, Vol. 33, pp.

377–381 (1990)). Isolated chromosomes were stained in 20 μg/ml of propidium iodide and analyzed or sorted using an EPICS Elite flow cytometer (Coulter). Chromosomes were sorted at the speed of 1,000 particles per minute by univariate flow sorting. Alternatively, chromosomes were separated prior to flow karyotype analysis in a 5–20% linear sucrose gradient in polyamine chromosome preparation buffer (Cram, L. S., et al, *Methods Cell Biol.*, vol. 33, pp. 377–381 (1990)) and separated by centrifugation at 80 g for 1 hr using a swinging bucket rotor (Beckman).

C. DNA analysis. For slot blot analysis, DNA was isolated from the sorted and the unsorted chromosomes by extraction with phenol-chloroform and precipitation with ethanol. DNA was then transferred to a nylon filter (Hybond-N$^+$, Amersham) using a slot blot mold (Schleicher & Schuell) and hybridized in 5× SSPE (0.9M NaCl, 50 mM NaHaPO4, 5 mM EDTA, pH 7.4), with 100 μg/ml sheared salmon sperm DNA at 65° C. using a human Alu probe (Deininger, P. L., *J. Mol. Biol.*, Vol. 151, pp. 17–33 (1981)) prepared by random priming (Feinberg, A. P., *Anal. Biochem.*, Vol. 132, pp. 6–13 (1983)), or at 50° C. using an end-labeled (Chaconas, G., *Methods Enzymol.*, Vol. 65, pp. 75–85 (1980)) muntjac repeat probe (Bogenberger, J. M., *Eur. J. Biochem.*, Vol. 148, pp. 55–59 (1985)). Filters were washed three times with 2× SSPE, 1% SDS for 20 min at the hybridization temperature and then autoradiographed.

To test the size of either sorted or unsorted chromosomes, agarose blocks of chromosomes were prepared in 1% low melting temperature agarose (Koi, M., *Science*, Vol. 260, pp. 361–364 (1993)) and analyzed by CHEF electrophoresis. The DNAs were separated on a 1% agarose gel using a BioRad CHEF Mapper in 0.5× TBE(89 mM Tris-HCl, 89 mM boric acid, and 2 mM EDTA) at 14° C. for 27 hours at 6 V/cM using a 120° C. angle with a 60 second switch time for 15 hours, and a 90 second switch time for 12 hours. *Saccharomyces cerevisiae* chromosomes were used as size markers. DNA was then transferred to nylon filters. Filters were hybridized with a human Alu probe (Deininger, P. L., *J. Mol. Biol.*, Vol. 151, pp. 17–33 (1981)) and visualized by autoradiography.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A female muntjac cell which has been immortalized with a nonviral vector, chemical treatment, or radiation treatment, wherein said female muntjac cell is diploid and has a normal female muntjac karyotype of 2n=6.

2. The female muntjac cell of claim 1, which is karyotypically stable for at least 15 passages.

3. The female muntjac cell of claim 1, which is karyotypically stable for at least 100 passages.

4. The female muntjac cell of claim 1, which is karyotypically stable for at least 3 months.

5. The female muntjac cell of claim 1, which is karyotypically stable for at least 18 months.

6. The female muntjac cell of claim 1, wherein said female muntjac cell is immortalized with pSV3gpt, pSV3neo, a vector containing an oncogene, or E1A.

7. The female muntjac cell of claim 1, wherein said female muntjac cell is immortalized with pSV3gpt.

8. The female muntjac cell of claim 1, which is FM7.

9. A method of preparing an immortalized female muntjac cell, comprising immortalizing a female muntjac cell with a nonviral vector, a chemical treatment, or a radiation treatment, to obtain an immortalized female muntjac cell which is diploid and has a normal female muntjac karyotype of 2n=6.

10. The method of claim 9, wherein said female muntjac cell is obtained from an infant.

11. The method of claim 9, wherein said female muntjac cell is selected from the group consisting of a fibroblast cell and an epithilial cell.

12. The method of claim 9, wherein said female muntjac cell is a fibroblast cell.

13. The method of claim 9, where said female muntjac cell is immortalized with pSV3gpt, pSV3neo, a vector containing an oncogene, or E1A.

14. The method of claim 9, wherein said female muntjac cell is immortalized with pSV3gpt.

15. A hybrid cell, comprising (a) two copies of muntjac chromosome 1, (b) two copies of muntjac chromosome 2, (c) two copies of muntjac chromosome X, and (d) a nonmuntjac chromosome or nonmuntjac chromosome fragment, wherein said nonmuntjac chromosome or nonmuntjac chromosome fragment has a size of 25 to 500 Mb, wherein said hybrid cell is formed by introducing said nonmuntjac chromosome or nonmuntjac chromosome fragment into a female muntjac cell which has been immortalized with a nonviral vector, a chemical treatment, or a radiation treatment and is diploid and has a normal female muntjac karyotype of 2n=6.

16. The hybrid cell of claim 15, wherein said nonmuntjac chromosome or nonmuntjac chromosome fragment has a size of 50 to 300 Mb.

17. The hybrid cell of claim 15, wherein said nonmuntjac chromosome or nonmuntjac chromosome fragment is selected from the group consisting of human chromosomes, human chromosome fragments, mouse chromosomes, mouse chromosome fragments, rat chromosomes, rat chromosome fragments, cat chromosomes, cat chromosome fragments, dog chromosomes, dog chromosome fragments, horse chromosomes, horse chromosome fragments, pig chromosomes, pig chromosome fragments, avian chromosomes, avian chromosome fragments, amphibian chromosomes, amphibian chromosome fragments, insect chromosomes, and insect chromosome fragments.

18. The hybrid cell of claim 15, wherein said nonmuntjac chromosome or nonmuntjac chromosome fragment is selected from the group consisting of human chromosomes, human chromosome fragments, mouse chromosomes, and mouse chromosome fragments.

19. The hybrid cell of claim 15, wherein said nonmuntjac chromosome or nonmuntjac chromosome fragment is a human chromosome or a human chromosome fragment.

20. The hybrid cell of claim 15, wherein said nonmuntjac chromosome or nonmuntjac chromosome fragment comprises a selectable marker.

21. The hybrid cell of claim 20, wherein said selectable marker is selected from the group consisting of neo, hph, and gpt.

22. The hybrid cell of claim 20, wherein said selectable marker is neo.

23. A method for purifying a chromosome, comprising:
(i) forming a hybrid cell which comprises (a) two copies of muntjac chromosome 1, (b) two copies of muntjac chromosome 2, (c) two copies of muntjac chromosome X, and (d) a nonmuntjac chromosome or nonmuntjac chromosome fragment, wherein said nonmuntjac chromosome or nonmuntjac chromosome fragment has a size of 25 to 500 Mb and said nonmuntjac chromosome or nonmuntjac chromosome fragment comprises a selectable marker;

(ii) culturing said hybrid cell on a medium under a condition such that only a cell comprising said selectable marker will survive to obtain a substantially pure culture of said hybrid cell; and (iii) rescuing said nonmuntjac chromosome or nonmuntjac chromosome fragment from said hybrid cell;

wherein said hybrid cell is formed by introducing said nonmuntjac chromosome or nonmuntjac chromosome fragment into a female muntjac cell which has been immortalized with a nonviral vector, a chemical treatment, or a radiation treatment and is diploid and has a normal female karyotype of 2n=6.

24. The method of claim 23, wherein said nonmuntjac chromosome or nonmuntjac chromosome fragment has a size of 50 to 300 Mb.

25. The method of claim 23, wherein said female muntjac cell is immortalized with pSV3gpt, pSV3neo, a vector containing an oncogene, or E1A.

26. The method of claim 23, wherein said female muntjac cell is immortalized with pSV3gpt.

27. The method of claim 23, wherein said introducing is carried out by fusing a microcell which comprises said nonmuntjac chromosome or nonmuntjac chromosome fragment with said female muntjac cell which has been immortalized with a nonviral vector, a chemical treatment, or a radiation treatment.

28. The method of claim 23, wherein said female muntjac cell which has been immortalized is FM7.

29. The method of claim 23, wherein said selectable marker is selected from the group consisting of neo, hph, and gpt.

30. The method of claim 23, wherein said selectable marker is neo.

31. The method of claim 23, wherein said condition such that only a cell comprising said selectable marker will survive is selected from the group consisting of: (A) the presence of G418 in said medium; (B) the presence of hygromycin in said medium; and (C) the presence of mycophenolic acid in said medium.

32. The method of claim 23, wherein said condition such that only a cell comprising said selectable marker will survive is (A) the presence of G418 in said medium.

33. The method of claim 24, wherein said rescuing is carried out by a method selected from the group consisting of: (A) isolating said nonmuntjac chromosome or nonmuntjac chromosome fragment by flow cytometry; (B) isolating said nonmuntjac chromosome or nonmuntjac chromosome fragment by gradient centrifugation; (C) isolating said nonmuntjac chromosome or nonmuntjac chromosome fragment by zonal rotor centrifugation; (D) isolating said nonmuntjac chromosome or nonmuntjac chromosome fragment by swing bucket centrifugation; and (E) isolating said nonmuntjac chromosome or nonmuntjac chromosome fragment by centrifugal elutriation.

\* \* \* \* \*

UNITED STATES PATENT AND TRADEMARK OFFICE
CERTIFICATE OF CORRECTION

PATENT NO. : 5,635,376
DATED : JUNE 3, 1997
INVENTOR(S) : ANDREW P. FEINBERG et al

It is certified that error appears in the above-identified patent and that said Letters Patent is hereby corrected as shown below:

Column 4, line 59, "Radiaion" should read --Radiation--.

Column 9, line 14, "(1990).)," should read --(1990)),--

Signed and Sealed this

Ninth Day of June, 1998

Attest:

BRUCE LEHMAN

Attesting Officer

Commissioner of Patents and Trademarks